(12) United States Patent
Sarvestani

(10) Patent No.: US 12,702,493 B2
(45) Date of Patent: Aug. 11, 2026

(54) NAVIGATION SYSTEM HAVING A 3-D SURFACE SCANNER

(71) Applicant: B. Braun New Ventures GmbH, Freiburg im Breisgau (DE)

(72) Inventor: Amir Sarvestani, Freiburg (DE)

(73) Assignee: B. Braun New Ventures GmbH, Freiburg im Breisgau (DE)

( * ) Notice: Subject to any disclaimer, the term of this patent is extended or adjusted under 35 U.S.C. 154(b) by 209 days.

(21) Appl. No.: 18/729,288

(22) PCT Filed: Jan. 11, 2023

(86) PCT No.: PCT/EP2023/050566

§ 371 (c)(1),
(2) Date: Jul. 16, 2024

(87) PCT Pub. No.: WO2023/135178

PCT Pub. Date: Jul. 20, 2023

(65) Prior Publication Data

US 2025/0127574 A1 Apr. 24, 2025

(30) Foreign Application Priority Data

Jan. 17, 2022 (DE) ..................... 10 2022 100 923.8

(51) Int. Cl.
*A61B 34/20* (2016.01)
*A61B 34/10* (2016.01)
(Continued)

(52) U.S. Cl.
CPC ........ *A61B 34/20* (2016.02); *A61B 2034/105* (2016.02); *A61B 2034/2055* (2016.02);
(Continued)

(58) Field of Classification Search
CPC ..................................................... A61B 34/20
See application file for complete search history.

(56) References Cited

U.S. PATENT DOCUMENTS 9,913,733 B2 3/2018 Piron et al.
2003/0153978 A1* 8/2003 Whiteside ............. A61B 34/20 73/172
(Continued)

FOREIGN PATENT DOCUMENTS

DE 102011119608 A1 5/2013
DE 102021103411 A1 8/2022

OTHER PUBLICATIONS

Search Report received in German Application No. 10 2022 100 923.8 dated Oct. 13, 2022, with translation, 8 pages.
(Continued)

*Primary Examiner* — Christian A Sevilla
(74) *Attorney, Agent, or Firm* — Christopher A. Rothe; CM Law

(57) ABSTRACT

A surgical navigation system includes a tracking system for tracking the patient and preferably a medical instrument. A 3-D surface scanner can create a 3-D surface recording of an intracorporeal anatomy of the patient while being tracked by the tracking system. A control unit processes the 3-D surface recording and the pose of the tracked 3-D surface scanner and of the patient, determine a pose of the 3-D surface recording vis-à-vis the patient by way of the detected and tracked pose, complement a digital 3-D anatomy model of the patient with the 3-D surface recording at the determined pose, and output a view of the complemented digital 3-D model for surgical navigation that represents a current 3-D model for navigation. A system can include the navigation system and a surgical robot. A navigation method and a computer-readable storage medium can be used with the navigation system.

20 Claims, 3 Drawing Sheets

(51) Int. Cl.
*A61B 34/30* (2016.01)
*A61B 90/00* (2016.01)

(52) U.S. Cl.
CPC ... *A61B 2034/302* (2016.02); *A61B 2090/373* (2016.02); *A61B 2090/3916* (2016.02)

(56) References Cited

U.S. PATENT DOCUMENTS

2006/0281971 A1* 12/2006 Sauer .................... A61B 34/20 600/101
2013/0162775 A1* 6/2013 Baumann ............... A61B 5/065 348/45
2019/0142524 A1* 5/2019 Hladio ...................... G06T 7/30 600/249
2020/0015911 A1* 1/2020 Yi .......................... A61B 34/10

OTHER PUBLICATIONS

Search Report received in International Application No. PCT/EP2023/050566 dated Mar. 28, 2023, with translation, 7 pages.
Written Opinion received in International Application No. PCT/EP2023/050566 dated Mar. 28, 2023, with translation, 15 pages.

* cited by examiner

NAVIGATION SYSTEM HAVING A 3-D SURFACE SCANNER

CROSS-REFERENCE TO RELATED APPLICATIONS

This application is the United States national phase entry of International Application No. PCT/EP2023/050566, filed on Jan. 11, 2023, and claims priority to German Application No. 10 2022 100 923.8, filed on Jan. 17, 2022. The contents of International Application No. PCT/EP2023/050566 and German Application No. 10 2022 100 923.8 are incorporated by reference herein in their entireties.

FIELD

The present disclosure relates to a surgical navigation system for navigation during a surgical intervention on a patient, in particular during knee-joint surgery. In addition, the present disclosure relates to a surgical assistance system, a navigation method and a computer-readable storage medium.

BACKGROUND

Current surgical navigation systems can be substantially divided into two groups/types/classes or kinds of surgical navigation systems.

The first group of navigation systems is an image-supported or picture-supported navigation and uses images such as computed tomography images (CT images), magnetic resonance images (MR images), X-ray images or ultrasound images, which are created and stored preoperatively before the intervention to be performed. These images then have to be compared with the patient's pose before and during the intervention to enable navigation of instruments or implants.

The second group of navigation systems is imageless or pictureless navigation and works without (preoperative) images. This second group of navigation systems creates a rudimentary (geometric) virtual or digital model of the patient up-to-date during the intervention on the patient and is usually performed by sweeping anatomical landmark points or orientation points with a navigation probe, a pointer or, for example, through a kinematic analysis. Such a 3D anatomy model digitally reproduces important anatomical points in a computer-aided system to enable navigation for the surgeon.

However, the disadvantage of image-based navigation systems is that they require complex and time-consuming registration, which often does not provide the required accuracy, in particular in the case of knee surgery or craniotomy.

In contrast, the second group of imageless navigation systems does not require preoperative imaging or intraoperative registration, but the second group has the disadvantage that they only use a very rough, rudimentary digital 3D model of the patient's anatomy (digital 3D anatomy model) as a reference, for example an axis model of the leg during knee surgery. The real three-dimensional (3D) structure of the leg is simplified and modeled using straight lines (two-dimensional structure) in (three-dimensional) space in order to obtain at least a rough 3D (overview) model of the leg. This geometric schematic 3D model can then be viewed in a computer-aided system from different angles.

SUMMARY

It is therefore the objects and objectives of the present disclosure to avoid or at least reduce the disadvantages of the prior art and, in particular, to provide a surgical navigation system, a surgical assistance system, a navigation method and a computer-readable storage medium which enables improved, more flexible navigation and, in particular, does not require preoperative imaging/image with subsequent intraoperative registration, but provides a sufficiently accurate intracorporeal 3D image of the patient for an intervention region of interest of the patient as a reference for navigation in order to be able to align instruments or implants, for example. In particular, the aim is to provide even better, faster, more flexible and more accurate navigation with a navigation system that is as easy to use as possible, allowing intraoperative three-dimensional detection and visualization of anatomical structures of interest of an intervention region.

Thus, a basic idea of the present disclosure is that the surgical navigation system comprises, in particular consists of: a following system/tracking system (with in particular a navigation camera) for locating or localizing (a pose of) at least one body portion of the patient on which the intervention is performed, and a 3D surface scanner. Furthermore, the navigation system may preferably have medical instruments for the intervention. The 3D surface scanner, in particular a 3D surface scanner camera, is used during an intervention to create a 3D surface image intraoperatively after opening the patient and to use this to create a digital 3D surface model of the patient's internal anatomy (digital 3D anatomy model of the patient) or to supplement an existing 3D anatomy model of the patient, which ultimately serves as a reference for navigation and, in particular, can be used by instruments or implants for guidance to their target position.

In particular, the surgical navigation system according to the present disclosure comprises a following system, in particular with a navigation camera, preferably one or more trackers for following the patient and preferably one or more trackers for following/tracking instruments or implants. In addition, the navigation system comprises a 3D surface scanner which can be tracked by the following system/tracking system (or the pose is detectable in space) and in particular is equipped with a tracker/marker in order to (indirectly) detect and localize (via the tracker) the position, in particular the position and orientation (i.e. the pose), of the scanned intracorporeal anatomical 3D surface with the following system (the navigation camera). Since the tracking system detects both the pose of the body portion of the patient and the pose of the 3D surface image, a relative transformation of the patient (or the body portion of interest) to the 3D surface image can be established and a pose of the 3D surface image can be correlated to the patient. The 3D surface scanner targets or is aligned with the anatomical region of interest and detects a 3D surface image of this region. This provides it with a digital 3D surface model, which it integrates into a 3D anatomy model of the patient. This 3D surface image can also be extended to include other anatomical regions by moving the 3D surface scanner, for example manually by hand or controlled by a robotic arm. During (i.e. at the same time as) the detection of the real anatomical 3D surface as a (digital) 3D surface image, the 3D surface scanner, in particular a 3D scan camera, is localized in space (position and/or orientation) and the 3D surface image is correlated with the patient on this basis, in particular with the help of a patient tracker provided on the patient. In particular, the position and/or orientation of the 3D surface image relative to the patient is determined. In other words, the navigation system thus comprises in particular: a tracking system (localization system), at least one tracker attached to the patient and a 3D surface scanner equipped with a tracker, wherein the 3D surface scanner, in particular as a 3D surface scanning camera, creates a 3D surface image of a targeted internal anatomy of the patient and the 3D surface scanner is localized relative to the patient. The 3D surface image is transmitted to a control unit or a computer system. The navigation system has an output device, in particular a display, and the 3D anatomy model supplemented by the 3D surface image can be used as a reference for positioning navigated instruments or implants without having to use preoperative images of the patient.

This 3D surface image (as a generated 3D surface) is provided to a control unit or transferred to an adapted computer system (as a control unit). The navigation system furthermore has an output device for a visual output, in particular a display (such as an operating theater monitor). The control unit or the computer system creates and supplements a digital three-dimensional (3D) anatomical model of the patient (3D anatomy model of the patient), which can optionally be supplemented by palpation/palpated anatomical landmark points or in which landmark points are already present. The computer system or control unit then enables the planning and navigation of the intervention, for example by visually positioning an orthopedic prosthesis in a target pose. During the intervention, the navigation system of the present disclosure then displays the current position and/or orientation, in particular pose, of navigated instruments or implants relative to the 3D anatomy model of the patient with optionally includable and displayable intervention plan, so that a surgeon can optimally guide and position the instruments or implants to achieve the best result for the patient.

The present surgical navigation system can thus combine and make the best possible use of the advantages of the technologies of image-based navigation and imageless navigation, so that the surgical navigation system does not require a preoperative image/imaging with subsequent intraoperative registration, but still has an accurate 3D model (3D anatomy model) of the patient as a reference, in particular to align instruments or implants in the best possible way for the best possible intervention result. The surgical navigation system demonstrates its advantages in particular in orthopedic navigation, where the exact shape and arrangement of bones have to be recorded and made available for navigation.

In yet other words, a surgical navigation system for use in a surgical intervention on a patient is disclosed, comprising: a tracking system/following system/localization system adapted to detect and track at least the body portion of the patient of interest on which the intervention takes place, in particular the entire patient, and preferably at least one medical instrument, with respect to its pose; a 3D surface scanner adapted to create a 3D surface image (in a sense a 2D surface structure in 3D space) of an intracorporeal anatomy of the patient of interest, wherein the 3D surface scanner is tracked by the tracking system, in particular via an attached tracker; and a control unit adapted/configured: to process the 3D surface image and the detected and tracked pose of the tracked 3D surface scanner and of the tracked patient (or their body portion), to determine a position and orientation (i.e. pose) of the 3D surface image relative to the patient via the detected and tracked pose of the 3D surface scanner, and to supplement a virtual, digital 3D anatomy model of the patient (or at least a digital 3D anatomy model of the body portion of interest), which is stored in particular in a storage unit, at the specific position and orientation (i.e. pose) with the (local) 3D surface image (in a correlated manner), and to visually output a view of the supplemented digital 3D anatomy model of the patient for surgical navigation via an output device, in particular an operating theater monitor, in order to provide an up-to-date digital 3D anatomy model supplemented with the intracorporeal anatomy of the patient of interest for navigation.

The 3D surface scanner of the navigation system can work at high speed and with high precision, is cost-efficient, easy to handle and particularly suitable for use in the field of medical technology. These advantages therefore also extend to the navigation system. In particular, a 3D surface scanner with structured light can be used in spinal and neuro navigation to create a 3D surface image of a targeted patient's anatomy during the intervention. This can preferably also be used to register a preoperative data set such as a CT image or an MR image taken before the intervention. In particular, the 3D surface scanner can be used to create a 3D point cloud and, preferably, to overlay a color map.

This surgical navigation system can be used for various indications. In knee surgery, for example, it can be used to create a 3D surface image of the joint surface of the knee joint after opening and exposing the knee. In particular, this 3D surface image of the distal femur can be detected relative to a reference of a femur tracker, while a 3D surface image of the proximal tibia can be detected relative to a reference of the tibia tracker. The 3D surface image of the thigh bone (femur) and shin bone (tibia) can optionally be supplemented by anatomical points of orientation such as the hip center, knee center and patella center, tibia center and ankle center, or a 3D anatomy model of the patient with existing anatomical points of orientation can be supplemented by the 3D surface image. Once the at least one 3D surface image(s) and preferably anatomical landmarks have been detected, a knee prosthesis in particular can be positioned in the intended alignment with the biomechanical axes. The 3D surface images of the femur and tibia enable particularly precise positioning and sizing of the prosthesis.

In the case of hip surgery, for example, the surgical navigation system can create a 3D surface image of the acetabulum and supplement the imageless, landmark-based digital 3D anatomy model of the patient with the 3D surface image of the acetabulum. This makes it possible not only to visualize the anatomical angles and distances during socket alignment, but also to visually check the fit and alignment of the socket implant relative to the bone structure. The term "position" means a geometric position in three-dimensional space, which is specified in particular via coordinates of a Cartesian coordinate system. In particular, the position can be specified by the three coordinates X, Y and Z.

The term "orientation" in turn indicates an orientation (such as position) in space. It can also be said that the orientation indicates an indication of direction or rotation in three-dimensional space. In particular, the orientation can be specified using three angles.

The term "pose" includes both a position and an orientation. In particular, the pose can be specified using six coordinates, three position coordinates X, Y and Z and three angular coordinates for the orientation.

The term 3D defines that the image data is spatial, i.e. three-dimensional. The patient's body or at least a part of the body with a spatial extension may be digitally available as image data in a three-dimensional space with a Cartesian coordinate system (X, Y, Z), for example.

Advantageous embodiments are explained in particular below.

According to an embodiment, the 3D surface scanner of the navigation system may comprise a handle and preferably a wireless communication module (such as WIFI, Bluetooth or IR) for manually guiding the 3D surface scanner and creating 3D surface images in different poses. In particular, the 3D surface scanner with handle may have a battery to act as a self-sufficient module. Alternatively or additionally, the 3D surface scanner may have a mounting portion, in particular a clamping module, in order to be attached to a holding arm of the navigation system in particular. Alternatively or additionally, the surgical navigation system may comprise a robot with a robot arm to which the 3D surface scanner is connected as an end effector in order to automatically create the 3D surface image in at least one predefined pose of the 3D surface scanner, in particular in order to create multiple 3D surface images in multiple poses of the 3D surface scanner, preferably according to a sweeping algorithm or sweeping pattern. In other words, in particular, the 3D surface scanner may be configured to be held in the hand, to be mounted on a static mechanical holding arm of the navigation system or to be held and actively moved by a robotic arm. In particular, the 3D surface scanner may be attached to a robotic arm of the navigation system or of the assistance system, which moves the 3D surface scanner autonomously to detect the anatomical area of interest (controlled).

According to a further embodiment, the 3D surface scanner may have an emitter for structured light and a sensor, in particular an RGB sensor (for example a camera) for detecting the light and/or may have a stereo camera and/or may have a time-of-flight camera and/or may have a LIDAR scanner, in particular in order to create a 3D point cloud of the anatomical region of interest as a 3D surface image. In other words, the 3D surface scanner can thus create the 3D surface images using various technologies, in particular with structured light and corresponding detection, with a stereo camera (stereo vision), with a time-of-flight camera or a LIDAR sensor/lidar camera, in order to create, in particular, a 3D point cloud of the anatomical region of interest.

Preferably, the tracking system and/or the control unit and/or the 3D surface scanner of the navigation system is adapted to determine a pose using machine vision. In particular, a 2D camera is used to create images from different viewing directions relative to the object or surface of interest and spatial information is calculated from these images.

Preferably, the tracking system may have an optical tracking system and/or a tracking system/localization system based on machine vision and/or an EM tracking system. In particular, the navigation system may be configured to perform electromagnetic following (EM navigation system) in addition to the optical tracking system.

Preferably, a virtual digital 3D anatomy model of a leg portion of the patient including the knee may be stored in a storage unit of the navigation system and the navigation system with the 3D surface scanner may be adapted to create a 3D surface image of the knee joint, wherein the navigation system for this purpose comprises a tibia tracker and a separate femur tracker adapted to be rigidly arranged on the tibia and on the femur for a following of the bone. The control unit is adapted to correlate the 3D surface image to the tracked leg portion based on the tracked tibia tracker and femur tracker. Two bone references (bone portion tibia and femur in the area of the knee joint) are thus tracked separately with the navigation, wherein two or more 3D surfaces of the anatomy are detected relative to the corresponding reference bones. In particular, the navigation system may thus be adapted to track two reference bones with respective trackers attached separately with the tracking system and to create at least two intracorporeal anatomical 3D surface images relative to the reference bones.

According to an embodiment, the control unit may be adapted to supplement the digital 3D anatomy model of the patient by landmark points, in particular hip center, knee center and patella center, tibia center and/or ankle center, in particular via a pointer of the navigation system, in order to obtain a combined digital 3D anatomy model of points, (biomechanical) axes, and surfaces. In other words, the detected 3D surface may be supplemented with additional anatomical landmark points/landmarks detected on the patient by sweeping or kinematic movements, resulting in a combined model of points, (biomechanical) axes and surfaces.

According to a further embodiment, the control unit may be adapted to process at least two 3D surface images in at least two different (detected) poses of the 3D surface scanner in order to obtain an extended and/or more precise 3D surface image as a total image on the basis of these individual 3D surface images. This technique, also known as stitching technology, combines several individual 3D surface images to form a total image. Similar to a panorama function in photos, several images are linked together, in particular at overlapping areas. However, the pose detected by the 3D surface scanner does not necessarily mean that there is an overlapping area, as individual separate regions can also be added. The navigation system therefore allows an absolute addition and does not require a relative reference. Preferably, the control unit may be adapted to calculate a resulting 3D surface image for this area at overlapping areas of 3D surface images in order to increase precision. In particular, the 3D surface image may be detected in a single static position, in particular pose, or across multiple positions, in particular poses, thereby increasing the scanned surface area and thus the 3D anatomy model of the patient.

Preferably, the 3D surface scanner may be adapted to be inserted intracorporeally into the patient, and in particular may have a maximum width and a maximum height, particularly preferably a maximum dimension, of 10 cm. The 3D surface scanner, in particular 3D surface scanner camera, can thus be small enough to be inserted inside the patient's anatomy in order to detect surfaces of a deep lying region as 3D surface images. The detected 3D surface image can be used to plan the position of an implant or instrument during surgery.

In particular, the surgical navigation system may have a surgical endoscope in which the 3D surface scanner is integrated, in particular in its front/end-side endoscope head. The 3D surface scanner may therefore be a (component) part of a surgical endoscope.

According to an embodiment, the 3D anatomy model of the patient with an implant according to the intervention plan may be stored in a storage unit of the navigation system, and the control unit may be adapted to intraoperatively verify the pose of the real implant against the pose of the implant according to the intervention plan via a 3D surface image with the 3D surface scanner, and to issue a warning via the display device in the event of a deviation. The 3D surface scanner can therefore also be used after the implant has been inserted to check the position and compare it with the intervention plan. In particular, the control unit compares a target pose of the implant in the 3D anatomy model of the patient with an actual pose according to the 3D surface image performed and a deviation is displayed via the output device in order to provide the surgeon with information regarding the alignment.

In particular, the control unit may be adapted to supplement the 3D surface image in the digital 3D anatomy model of the patient as featureless surfaces or as a surface with color texture or with grayscale texture. In other words, the 3D surface image may preferably be converted and stored in the form of a featureless surface or a surface with color or grayscale texture.

According to an embodiment, the control unit may be adapted to recognize predefined structures of interest in the 3D surface image, in particular to recognize bones, and to supplement the digital 3D anatomy model only with these predefined structures of interest to. In particular, the detected 3D surface images may therefore be manipulated in such a way that only structures of interest remain in the 3D surface image. Structures that do not belong to the bone, such as the skin, are automatically delimited from the 3D surface image.

With regard to a surgical assistance system, the objects are solved in that it comprises a navigation system according to the present disclosure and a medical robot with a medical end effector. In particular, the navigation system can be integrated into a surgical robot without the need for a preoperative image volume. Accordingly, the surgical assistance system can be used to provide the data for navigation via the navigation system and an automated or semi-automated intervention can be performed via the robot with the end-effector. In knee surgery in particular, the robot can be controlled on the basis of the created and supplemented 3D anatomy model of the patient so that the end-effector performs a resection of the tibia and femur and also preferably inserts a knee prosthesis automatically in a pose-correct manner.

With regard to a navigation method for use in a surgical intervention in a patient, in particular in knee arthroplasty, preferably in a surgical navigation system of the present disclosure, the objects are solved in that the navigation method comprises the steps:

- following a patient and preferably at least one medical instrument, in particular a pointer, via a tracking system/following system;
- creating a 3D surface image of an intracorporeal anatomy of the patient of interest by a 3D surface scanner and following the 3D surface scanner by the tracking system, in particular via attached trackers;
- determining, via the detected pose of the 3D surface scanner, a pose of the 3D surface image in relation to the patient;
- supplementing a digital 3D anatomy model of the patient at the specific pose with the 3D surface image (correlated); and
- outputting a visual view of the supplemented digital 3D anatomy model of the patient for surgical navigation via an output device, in particular via an operating theater monitor, in order to provide an up-to-date digital 3D anatomy model supplemented with the intracorporeal anatomy of the patient of interest for navigation. Using this navigation method, an intervention can be performed quickly, easily and flexibly, in particular knee-joint surgery with a knee prosthesis, and patient safety can be further improved.

In particular, the navigation method may further comprise the steps of creating a 3D surface image of a front face of a femur in a first pose of the 3D surface scanner, in particular via a robot-guided 3D surface scanner; detecting the pose of the 3D surface scanner and a femur via a femur tracker (on the femur) by the tracking system; creating a 3D surface image, in particular of a front face, of a tibia in a second pose of the 3D surface scanner, in particular in a robot-guided manner; detecting the pose of the 3D surface scanner and of a tibia via a tibia tracker on the tibia by the tracking system; and supplementing the digital 3D anatomy model of the patient with the 3D surface images at the specific pose (pose-correct integration of the digital image data) by the control unit.

With respect to a computer-readable storage medium, the objects are solved by comprising instructions which, when executed by a computer, cause the computer to perform the method steps of the navigation method according to the present disclosure.

The disclosure with respect to the navigation system according to the present disclosure applies also to the navigation method according to the present disclosure and vice versa. In particular, the control unit of the navigation system may be adapted to (such as having a processor and a storage unit with instructions) perform the method steps according to the navigation method.

BRIEF DESCRIPTION OF THE DRAWINGS

The invention is explained in more detail below with reference to preferred embodiments with the aid of Figures.

The Figures are schematic in nature and are only intended to aid understanding of the invention. Identical elements are marked with the same reference signs. The features of the various embodiments can be interchanged.

DETAILED DESCRIPTION

Figure 1:
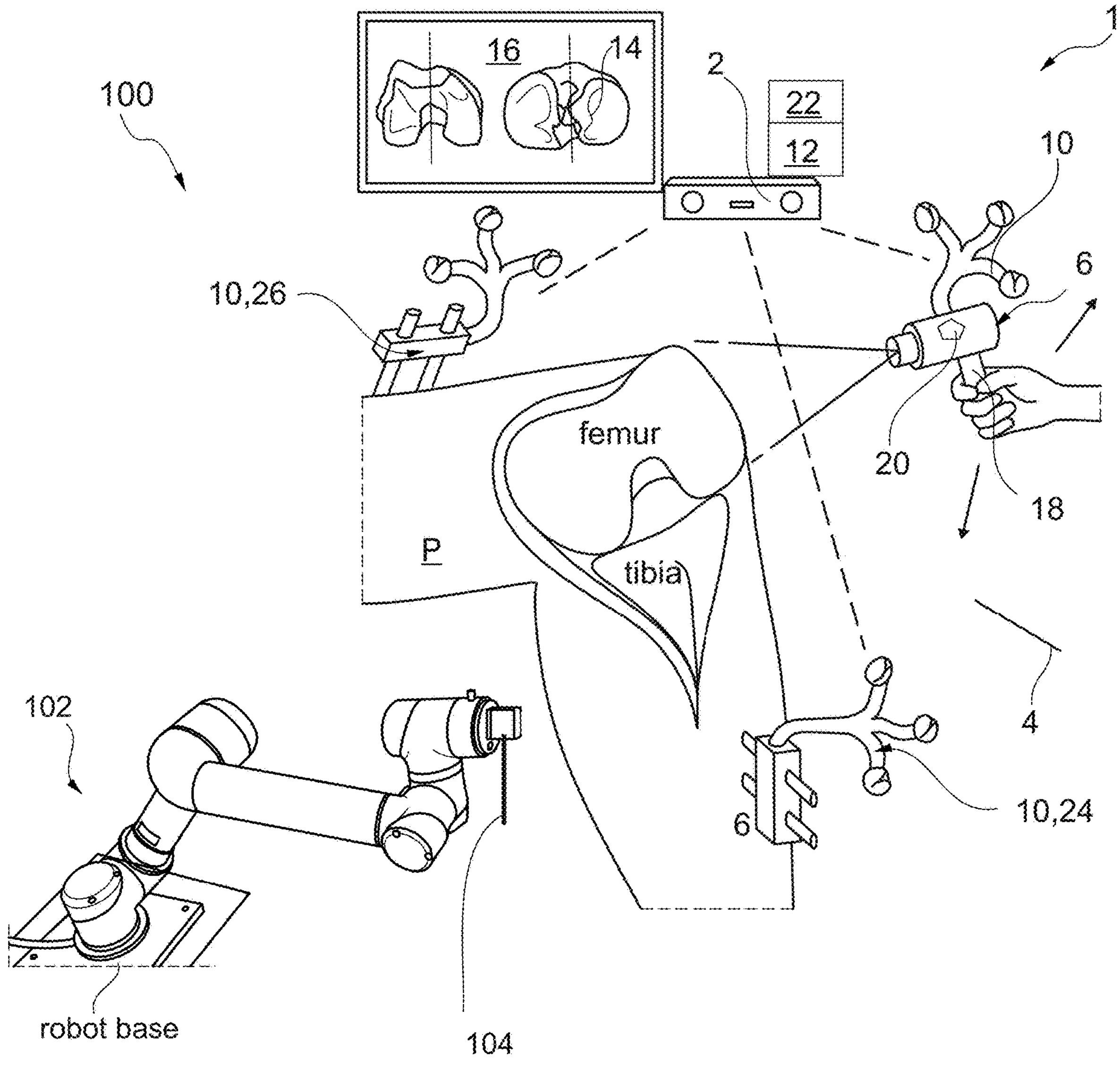
FIG. 1 shows a perspective, schematic view of an assistance system with a surgical navigation system according to a preferred embodiment of the present disclosure, which is adapted for knee surgery.

FIG. 1 shows a schematic perspective view of a surgical assistance system 100 according to a preferred embodiment with a robot 102 and a surgical navigation system 1 according to a preferred embodiment.

The surgical navigation system 1 is used for a surgical knee operation on a patient P, in which a resection of a tibia is performed and an implant is inserted into the knee joint. Accurate and up-to-date navigation is crucial for this surgical intervention on the patient.

The navigation system 1 has an optical tracking system 2 for detecting a pose of a solid body, which is adapted to detect and track the patient P and also a medical instrument with an attached solid body. In this embodiment, the tracking system 2 has a stereo camera for three-dimensional detection and a downstream processing unit to determine a pose in space on the basis of the stereo image. The solid body to be detected by the tracking system 2 is in the form of a tracker 10 with three spaced-apart spheres, so that the tracking system can indirectly deduce the pose of the associated portion to which the tracker 10 is attached via the detection of the pose of the tracker 10.

The navigation system 6 furthermore has a mobile, handheld 3D surface scanner 6, which is specially adapted to create a 3D surface image 8 of an intracorporeal anatomy of the patient P of interest, in this case of the knee joint with the corresponding bones. The 3D surface scanner 6 itself is tracked by the tracking system 2 via an attached tracker 10, so that a pose of the 3D surface scanner 6 in space is determinable by the tracking system 2. In other words, the 3D surface scanner 6 records a three-dimensional surface of a knee joint of the patient P (with color information and, to a certain extent, height information, similar to that of a three-dimensional map), wherein the pose of the 3D surface scanner 6 is detected during the 3D surface image 8. Since the pose of the 3D surface image 8 to the pose of the 3D surface scanner 6 is determinable, and further, the pose of the 3D surface scanner to the stereo camera of the tracking system 2, a transformation between the 3D surface image 8 and the tracking system is also determinable.

Since the knee joint of the patient P is furthermore detected via the tracker 10 (here the femur and the tibia), the pose of the leg as the body portion of the patient is also determinable in relation to the tracking system 2 and a transformation from the pose of the individual bones to the local coordinate system (KOS) of the tracking system 2 is determinable. This means that the pose (of the local KOS) of the femur and the pose (of the local KOS) of the tibia and thus of the knee joint in relation to the 3D surface image 8 can be determined by linking the two transformations.

Specifically, a control unit 12 with a processor, a RAM module, and a storage is adapted to process the 3D surface image 8 and the detected and tracked pose of the 3D surface scanner 6 and of the patient P and to determine a pose of the 3D surface image 8 relative to the patient P via the pose of the 3D surface scanner 6 and to supplement a virtual, digital 3D anatomy model 14 of the patient P at the specific pose with the 3D surface image 8. By detecting the real leg of the patient P by the tracking system 2, a correlation of a virtual model of the leg of the patient P with the real leg can be carried out, so that the pose of the 3D surface image 8 to the pose of the virtual leg is also determinable. It can also be said that a 3D anatomy model 14 of patient P is stored in the virtual or digital space, for example as a schematic biomechanical axis model (axis with start and end point as a representation of a bone) with further landmark points, and this 3D anatomy model 14 of patient P is supplemented by the scanned surface of interest, i.e. the intervention region, in order to provide more detailed digital information on this intervention region and to support intraoperative navigation.

A view of the supplemented digital 3D anatomy model 14 of the patient P can then be output visually with computer support via a display as output device 16, for example an operating theater monitor, for surgical navigation in order to provide an up-to-date digital 3D anatomy model 14 supplemented by the intracorporeal anatomy of the patient P of interest for navigation. This eliminates the need for time-consuming registration and yet a 3D anatomy model 14 of the patient P can be provided, which offers particularly precise anatomical structural information for navigation in the area of the intervention.

The surgical navigation system 1 provides the special possibility that a 3D surface image 8 can be created in different poses and thus different viewing angles and views in order to expand the 3D anatomy model 14 of the patient P with regard to relevant recorded regions and also to further improve accuracy through redundant information and an optimization algorithm.

The 3D surface scanner 6 is configured in such a way that a surgeon can easily hold and guide it in his hand. For this purpose, the 3D surface scanner 6 has a handle 18 for manual gripping and guiding, as well as a rechargeable battery to provide self-sufficient energy and a radio communication module 20 in the form of a WLAN or Bluetooth module for data transmission to the control unit 12 in order to be wireless.

In another embodiment, not shown, the surgical navigation system can furthermore have a robot with a robot arm to which the 3D surface scanner 6 is connected as an end effector in order to automatically create the 3D surface image 8 in at least one predefined pose of the 3D surface scanner 6, in particular in order to create multiple 3D surface images 8 in multiple poses of the 3D surface scanner 6 according to a sweeping algorithm or sweeping pattern. If the 3D surface scanner 6 is robot-guided, an algorithm or predefined poses can be used to automatically move the 3D surface scanner 6 into these poses and create an image. This configuration would also have the advantage that a pose of the 3D surface scanner 6 is not only detectable via a tracker, but also via kinematics in relation to a robot base, wherein a transformation between the robot base and the tracking system is determinable. In this way, the pose of the 3D surface scanner 6 can be determined even if the view of the tracker is interrupted.

The virtual digital 3D anatomy model 14 of a leg portion of the patient P including the knee is stored in a storage unit 22 of the navigation system 1. The 3D surface scanner 6 creates the 3D surface image 8 of the knee joint, wherein the corresponding bone can be detected by the tracking system 2 via a separate tibia tracker 24 and femur tracker 26 that are rigidly screwed to the bone. The control unit 12 is adapted to correlate the 3D surface image 8 to the tracked leg portion on the basis of the tracked tibia tracker 24 and femur tracker 24.

Figure 2:
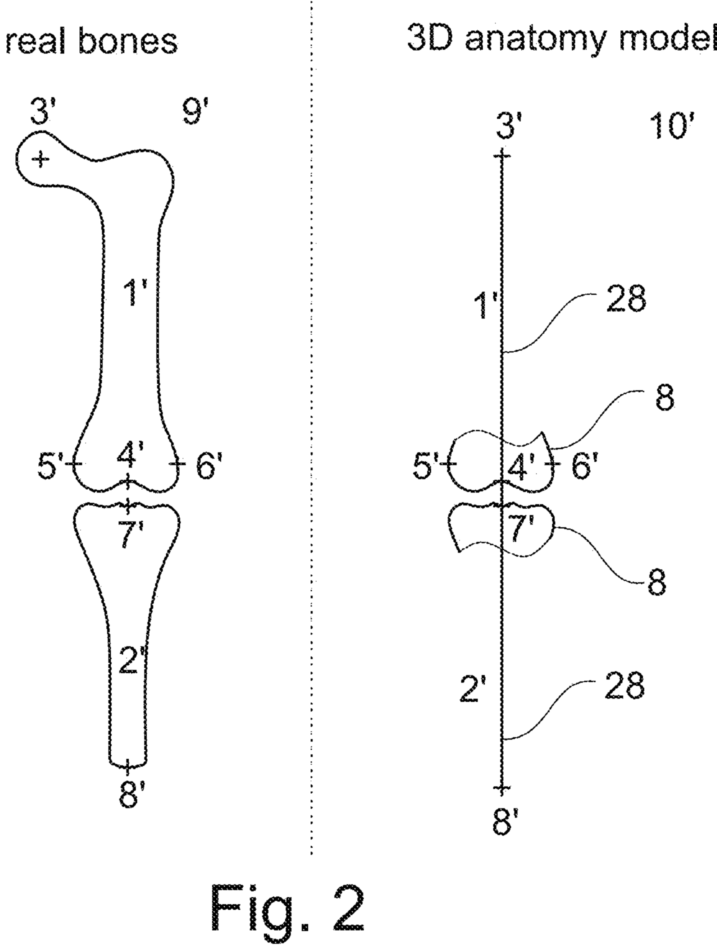
FIG. 2 shows a schematic 3D anatomy model of a patient with digitalized anatomical landmarks and a scanned 3D surface image of the knee surgery from FIG. 1.

FIG. 2 shows an example of the creation of a patient model or 3D anatomy model 14 based on a scanned 3D surface image and digitalized anatomical landmarks in the case of navigation during the intervention on the patient's knee shown in FIG. 1. The real bones of the patient are shown schematically on the left side in FIG. 2, while on the right side the 3D anatomy model 14 of the patient P is shown with straight biomechanical axes 28 (approximately) along a longitudinal axis of the two bones and with anatomical landmark points relevant for the intervention (in FIG. 2 supplemented with reference signs with a line for illustration purposes), in particular around the hip, knee and patella centers, tibia center and/or ankle center. On the real knee joint of patient P, the 3D surface scanner 6 creates a 3D surface image 8 locally as a partial section of the knee joint and this is added to the 3D anatomy model 14 of patient P as described above, indicated here by the inserted 3D surface on the right in FIG. 2.

Based on this 3D anatomy model 14 of patient P, the surgeon can then perform an operation and navigate accordingly, but also, when inserting an implant, compare a position of a target pose of the implant according to an intervention plan that reflects the target pose in the 3D anatomy model 14 of patient P with an actual pose of the implant and, if necessary, make corrections in order to adjust the actual pose to the target pose intraoperatively.

Figure 3:
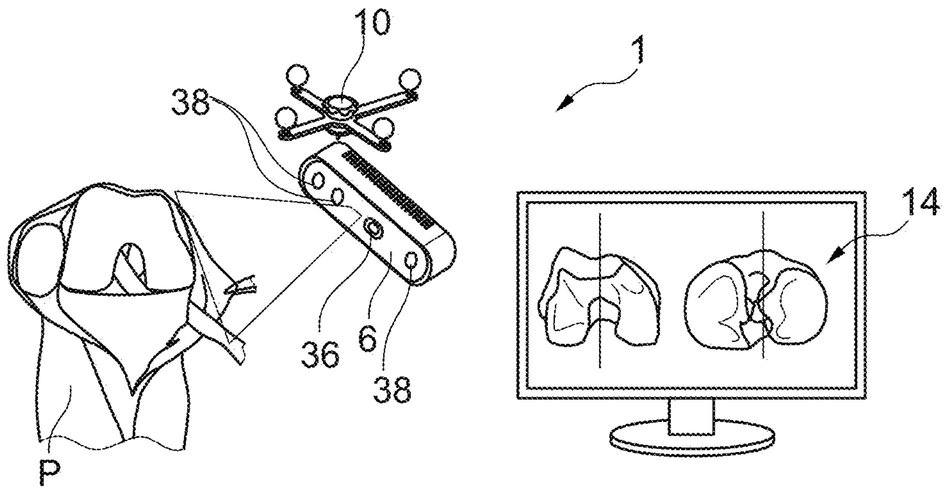
FIG. 3 shows a schematic perspective view of a 3D surface scanner of a navigation system of a further embodiment in the form of a 3D scan camera, which detects a joint surface of a knee joint and outputs a view of a 3D anatomy model via a screen.

FIG. 3 shows a surgical navigation system 1 according to another preferred embodiment. This uses a 3D camera with an emitter for structured light and several RGB sensors/RGB cameras as a 3D surface scanner 6. A solid body is again arranged on this as a tracker 10 in order to detect the pose via the tracking system 2. In its field of view 32, the 3D camera creates the surface image in the form of a point cloud in three-dimensional space in order to obtain the geometric information, and color information is also added according to the recorded color in order to make navigation even more intuitive. The knee joint is scanned with the 3D surface scanner 6 and the control unit 12 is adapted to recognize the bone from the 3D surface image and to determine only this as the relevant part of the 3D surface image and to add it to the 3D anatomy model 14 of the patient.

In this embodiment, the control unit 12 creates two views of the 3D anatomy model 14, one of the tibia and one of the femur, and displays them on a screen for navigation. This provides the surgeon with immediate and intraoperative information relevant to his intervention and enables him to perform an operation and to insert an implant even better.

Figure 4:
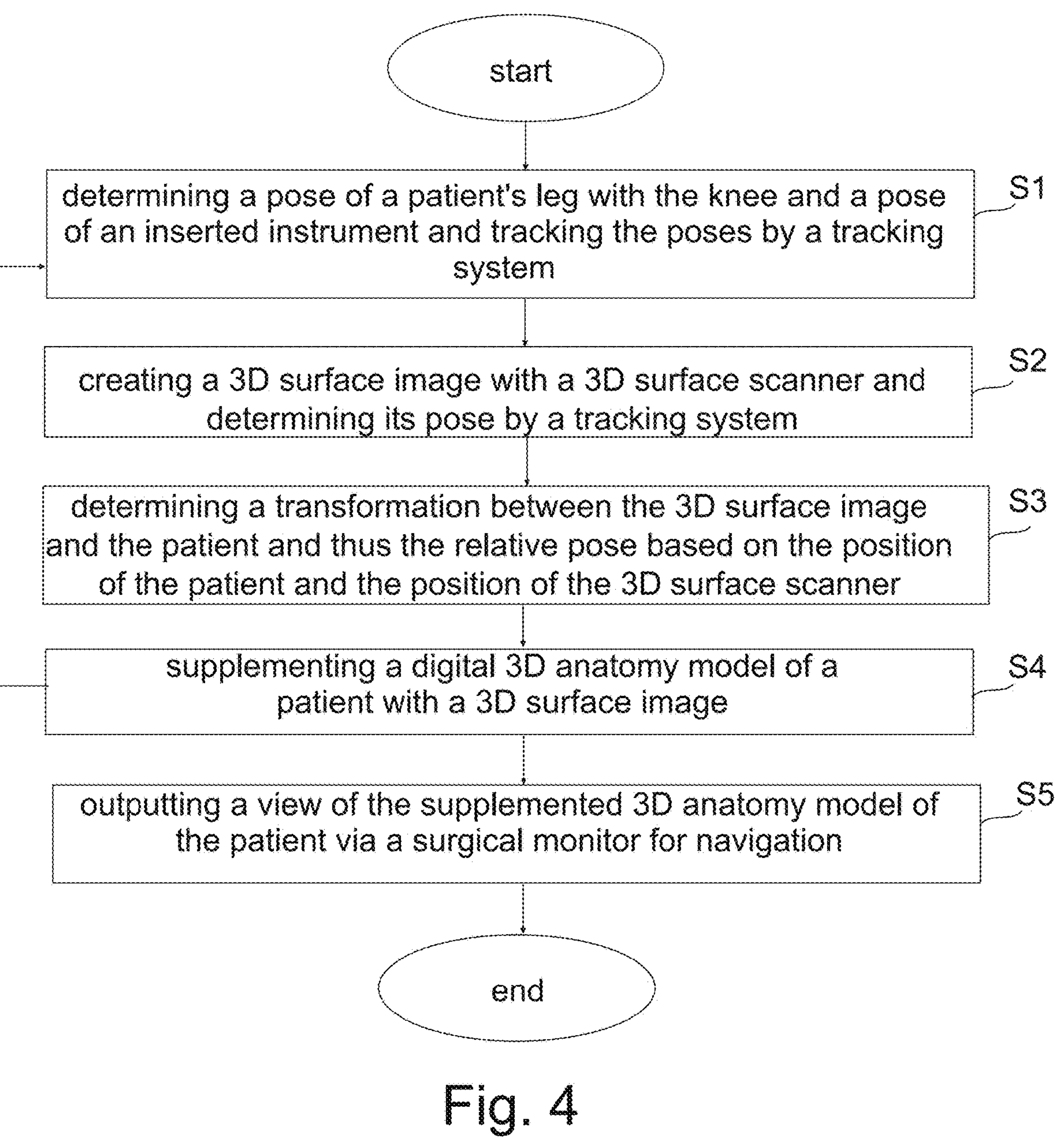
FIG. 4 shows a flow chart of a navigation method according to a preferred variant.

FIG. 4 shows a flowchart of a navigation method for use in a surgical intervention on a patient P, in particular a tibial resection.

In a first step S1, a pose of the leg of the patient P with the knee joint on which the intervention is performed and of a medical instrument used during the intervention is detected and tracked via a tracking system 2 of a navigation system 1. In particular, the pose is stored in the form of three position coordinates and three angles for an orientation.

In a step S2, a 3D surface image 8 of an intracorporeal anatomy of the patient P of interest is created with a 3D surface scanner 6 and a pose of the 3D surface scanner 6 is determined by the tracking system 2 at the time of the 3D surface image 8 via trackers 10 attached to the 3D surface scanner 6 and tracking in space.

In a subsequent step S3, a pose of the 3D surface image 8 with respect to the patient P is determined or calculated using the detected pose of the 3D surface scanner 6. In particular, a pose of the 3D surface image 8 relative to the 3D surface scanner 8 and further relative to the tracking system 2 and further relative to the patient P can be determined first. This transformation between the patient P and the 3D surface image is used by a control unit 12 to supplement the 3D surface image 8 with a digital 3D anatomy model (14) of the patient (P) at precisely this specific pose in a step S4. In other words, the virtual, digital 3D model of a body portion of the patient is supplemented by the 3D surface image 8 pose-correct.

Finally, a view of the virtually supplemented digital 3D anatomy model 14 of the patient P is created by the control unit 12, for example a front view, a side view, a perspective view, and this visual view of the supplemented digital 3D anatomy model 14 is then output or displayed for surgical navigation via an output device 16 in the form of an operating theater monitor 34 to provide an intraoperative, up-to-date digital 3D anatomy model 14 augmented with the intracorporeal anatomy of the patient (P) of interest for navigation.

LIST OF REFERENCE SIGNS

1 surgical navigation system
2 tracking system
4 medical instrument
6 3D surface scanner
8 3D surface image
10 tracker/marker
12 control unit
14 3D anatomy model
16 output device
18 handle
20 radio communication module
22 storage unit
24 tibia tracker
26 femur tracker
28 axis
30 landmark point
32 field of view
34 monitor
36 light source for structured light
38 RGB sensor
1', 2', 3', 4', 5', 6', 7', 8', 9' landmark points
100 surgical assistance system
102 robot
104 medical end-effector
P patient
S1 step of determining pose of the patient's leg and an instrument
S2 step of creating 3D surface image with 3D surface scanner and detecting pose of the 3D surface scanner
S3 step of determining a transformation between the 3D surface image and the patient
S4 step of pose-correct supplementing a 3D anatomy model with a 3D surface image
S5 step of outputting a view of the supplemented 3D anatomy model of the patient by an operating theater monitor

The invention claimed is:

1. A surgical navigation system for use in a surgical intervention on a patient, the surgical navigation system comprising:

a tracking system adapted to track at least the patient;

a 3D surface scanner adapted to create a 3D surface image of an intracorporeal anatomy of the patient, wherein the 3D surface scanner is tracked by the tracking system; and a control unit adapted to:

process the 3D surface image and a detected and tracked pose of the 3D surface scanner and of the patient, determine a pose of the 3D surface image relative to the patient via the detected and tracked pose of the 3D surface scanner, and to supplement a virtual, digital 3D anatomy model of the patient at a specific pose with the 3D surface image, and visually output a view of the virtual, digital 3D anatomy model of the patient for surgical navigation via an output device so that the virtual, digital 3D anatomy model is up-to-date and supplemented with the intracorporeal anatomy of the patient for navigation.

2. The surgical navigation system according to claim 1, wherein:

the 3D surface scanner comprises a handle, or the 3D surface scanner has a mounting portion, or the surgical navigation system comprises a robot with a robot arm to which the 3D surface scanner is connected as an end effector in order to automatically create the 3D surface image in at least one predefined pose of the 3D surface scanner.

3. The surgical navigation system according to claim 1, wherein the 3D surface scanner has an emitter for structured light and an RGB sensor for detecting the structured light and/or has a stereo camera and/or has a time-of-flight camera and/or has a LIDAR scanner.

4. The surgical navigation system according to claim 1, wherein the tracking system has an optical tracking system and/or has an EM tracking system.

5. The surgical navigation system according to claim 1, wherein the 3D surface scanner further comprises a wireless communication module for manually guiding the 3D surface scanner and creating 3D surface images in different poses.

6. The surgical navigation system according to claim 1, wherein:

the virtual, digital 3D anatomy model is of a leg portion of the patient including a knee, said virtual, digital 3D anatomy model being stored in a storage unit of the surgical navigation system, and the surgical navigation system is adapted to create a 3D surface image of a knee joint, the surgical navigation system comprises a tibia tracker and a femur tracker adapted to be rigidly arranged on a tibia and on a femur, respectively, for following a bone, and the control unit is adapted to correlate the 3D surface image to the leg portion based on the tibia tracker and the femur tracker.

7. The surgical navigation system according to claim 1, wherein the control unit is adapted to supplement the virtual, digital 3D anatomy model of the patient by landmark points in order to obtain a combined digital 3D anatomy model of points, axes, and surfaces.

8. The surgical navigation system according to claim 1, wherein the control unit is adapted to process at least two 3D surface images in at least two different poses of the 3D surface scanner in order to obtain an extended and/or more precise 3D surface image as a total image based on the at least two 3D surface images.

9. The surgical navigation system according to claim 1, wherein the 3D surface scanner is adapted to be inserted intracorporeally into the patient.

10. The surgical navigation system according to claim 1, wherein the surgical navigation system has a surgical endoscope in which the 3D surface scanner is integrated.

11. The surgical navigation system according to claim 1, wherein the virtual, digital 3D anatomy model of the patient with an implant according to an intervention plan is stored in a storage unit of the surgical navigation system, and the control unit is adapted to intraoperatively verify an actual pose of the implant against a pose of the implant according to the intervention plan via a 3D surface image with the 3D surface scanner, and to output a warning or deviation information via the output device when a deviation is present.

12. The surgical navigation system according to claim 1, wherein the control unit is adapted to recognize predefined structures of interest in the 3D surface image, and to supplement the virtual, digital 3D anatomy model only with the predefined structures of interest.

13. The surgical navigation system according to claim 1, wherein the tracking system is further adapted to track least one medical instrument.

14. The surgical navigation system according to claim 1, wherein the 3D surface scanner is tracked by the tracking system via an attached tracker.

15. The surgical navigation system according to claim 1, wherein the control unit is adapted to visually output the view of the virtual, digital 3D anatomy model of the patient for surgical navigation via an operating theater monitor.

16. A surgical assistance system comprising:

The surgical navigation system according to claim 1; and a medical robot with a medical end effector.

17. A navigation method for use in a surgical intervention in a patient, the navigation method comprising the steps of:

following a patient via a tracking system of a navigation system;

creating a 3D surface image of an intracorporeal anatomy of the patient by a 3D surface scanner and following the 3D surface scanner by the tracking system;

determining, via a detected pose of the 3D surface scanner, a pose of the 3D surface image in relation to the patient by a control unit;

supplementing a digital 3D anatomy model of the patient at a specific pose with the 3D surface image by the control unit; and outputting a visual view of the digital 3D anatomy model of the patient for surgical navigation via an output device in order to provide the visual view of the digital 3D anatomy model intraoperatively, up-to-date and supplemented with the intracorporeal anatomy of the patient for navigation.

18. The navigation method according to claim 17, wherein the navigation method further comprises the steps of:

creating a first 3D surface image of a front face of a femur in a first pose of the 3D surface scanner;

detecting the first pose of the 3D surface scanner and a femur tracker on the femur by the tracking system;

creating a second 3D surface image of a tibia in a second pose of the 3D surface scanner;

detecting the second pose of the 3D surface scanner and of a tibia tracker on the tibia by the tracking system;

supplementing the digital 3D anatomy model of the patient with the first 3D surface image and the second 3D surface image by the control unit.

19. The navigation method according to claim 18, wherein the 3D surface scanner is a robot-guided 3D surface scanner.

20. A computer-readable storage medium, comprising instructions which, when executed by a computer, cause the computer to perform the navigation method according to claim 17.

* * * * *